United States Patent [19]

Seitz

[11] Patent Number: 4,836,033

[45] Date of Patent: Jun. 6, 1989

[54] CAPACITIVE MEASURING ASSEMBLY FOR DETERMINING FORCES AND PRESSURES

[76] Inventor: Peter Seitz, Mohlstrasse 29, D-8000 Munchen 80, Fed. Rep. of Germany

[21] Appl. No.: 102,722

[22] Filed: Sep. 30, 1987

[30] Foreign Application Priority Data

Oct. 13, 1986 [DE] Fed. Rep. of Germany ....... 3634855

[51] Int. Cl.⁴ ................................................. G01D 7/02
[52] U.S. Cl. ............................. 73/862.04; 73/862.64; 361/291
[58] Field of Search ........... 73/862.04, 862.64, 862.68, 73/172; 901/33, 46; 361/280, 283, 291, 324

[56] References Cited

U.S. PATENT DOCUMENTS 3,678,378  7/1972  Trott et al. ...................... 361/283 X
4,437,134  3/1984  Nicol ................................... 361/283

FOREIGN PATENT DOCUMENTS 023732   2/1981  European Pat. Off. .
2529475  2/1981  Fed. Rep. of Germany .
3410955  9/1985  Fed. Rep. of Germany .
3411528 10/1985  Fed. Rep. of Germany .

Primary Examiner—Jerry W. Myracle
Attorney, Agent, or Firm—Burgess, Ryan & Wayne

[57] ABSTRACT

A capacitive measuring assembly for determining forces and/or pressures includes at least three plane parallel capacitor surfaces with intercalation of a dielectric therebetween. The capacitor surfaces being movable relative to each other against elastic resetting forces of the dielectric, a main surface being in opposing relation to all remaining surfaces and partly covering them with intercalation of the dielectric therebetween. The main surface being movable both perpendicular and parallel relative to the remaining surfaces so that from the individual capacity values between the main and remaining surfaces, there can be measured or eliminated both the forces that act perpendicularly between the main and remaining surfaces and the forces that act parallel with the capacitor surfaces.

23 Claims, 4 Drawing Sheets

CAPACITIVE MEASURING ASSEMBLY FOR DETERMINING FORCES AND PRESSURES

BACKGROUND OF THE INVENTION

The present invention is directed to a capacitive measuring assembly.

In many fields of technology, sports and medicine, it is necessary, in order to analyze specific phenomena to determine the forces that appear in a dynamic operation not only with regard to their total value, but also as to their distribution. Thus, for instance, it is extremely desirable for the manufacturer of automobile seats to know how the pressure distribution actually occurs on the surface and back rest of the seat when a person sits thereon in order that the seat can be made stronger or firmer in those places that bear a heavier load than in those places that bear a lighter load. In the manufacture of a ski, for example, it is desirable to know the force distribution in order to make it possible to adequately adapt the core construction to such distribution. Finally, in medicine, it is possible from the pattern of force distribution under the foot surfaces of a person being tested while walking to arrive at conclusions concerning orthopedic injuries or sensorial injuries as, for instance, in the case of diabetics, and to begin adequate therapeutical treatment.

For measuring the force distribution over surfaces, German Patent No. 25 29 475 discloses a matrix arrangement of lamellar capacitor elements disposed opposite to and intersecting each other with intercalation of an elastic dielectric. In this system, only vertical forces that is, only forces perpendicular to the capacitor surfaces, lead to measuring signals, since horizontal displacement of the lamellar capacitor elements effects no change of the surface dimensions opposite to each other. A disadvantage of such known system is the fact that the separate capacitor elements consisting of the surface sections directly opposite each other are mechanically interconnected so that local expansion is limited or measured patterns are adulterated.

It has been proposed in German Offenlegungsschrift No. 34 11 528 to uncouple the separate capacitor surfaces, to divide the lamellar capacitor surfaces into separate elements by notches, there being specially given in this publication, the suggestion of providing between the separate surfaces meandering current conductor paths through the corresponding notches. A very effective uncoupling of the separate surfaces is obtained by this arrangement in the sense that the pattern of force distribution to be measured is substantially more precise than formerly attained, but in this arrangement, forces parallel with the capacitor surface lead to a change of the effective capacitor surfaces, that is, to an adulteration of the vertical signal.

The above mentioned arrangements finally have in common that the three-dimensional measurement of force distribution that is desirable in many cases is not possible. For instance, it would be very interesting for the automobile tire industry, and of course also for all the other purposes described above, to know about the three-dimensional force distribution.

German Offenlegungsschrift No. 34 10 955 discloses a capacitive measuring system for determining forces wherein two groups of capacitor plates are disposed in a comblike arrangement and interlocked, being kept movable and parallel with each other. In the original state, when no forces act upon the capacitor plates or the fastening means thereof, the plates do not entirely overlap and thus, when relative forces are applied parallel with the surfaces of the plate sets, these become further interlocked whereby it is possible to measure an increase of capacity between the plates. In this arrangement, to avoid errors of measurement, the plates must be moved exclusively parallel with each other and thus, when using this known teaching, no three-dimensional force measurement is possible and it is not possible to eliminate forces in an inadmissible direction.

OBJECTS AND SUMMARY OF THE INVENTION

Departing from the above cited prior art, the problem to be solved by this invention is to develop a measuring assembly of the kind mentioned above in the sense of making possible, together with the measurement of force in one direction, an elimination or measurement of a force component in at least one other direction. Therefore, according to the instant invention, it is possible either to measure the forces acting in the dielectric due to the shearing effect and thus obtain a multi-dimensional measuring system or to disregard the result of the measuring, which is standard or common for the forces acting parallel with the surface in order to be able to more accurately determine the surface normal forces.

In a preferred embodiment of the invention where a specially simple compensation of surface parallel forces is possible, there is opposite to the main surface a smaller surface entirely covered by the former and quite substantially enclosed by a surrounding surface. The surrounding surface projects with its outer edge beyond the main surface so that the differential between the capacities of the surrounding surface and the main surface provides a standard for the horizontal forces which can be compensated by means of the capacity value between the main surface and the smaller surface in relation to the vertical force component or vice versa. Therefore, when importance is attached to the measurement of the surface parallel forces, what is obtained is not a statement concerning their direction but concerning their magnitude.

In another preferred embodiment of the invention, there are situated opposite the main surface, three or four substantially congruous smaller surfaces separated from each other with their outer edges projecting beyond the outer edge of the main surface. By an adequate calculation of the individual measured values, it is possible thus to determine the direction and amplitude of the resulting three-dimensionally seen force vector. The main surface and the mating surfaces are here preferably interconnected via capacity measuring elements and setups, the sum of the individual capacities corresponding to the vertical force and the sums or differentials of the individual capacities corresponding to the horizontal forces calculated on the total capacity or vertical force. The standardization of the horizontal or surface parallel forces by the vertical force is necessary because, in the measurement of the vertical force, the capacitor surface remains constant while the spacing between the capacitor plates varies, but upon the action of horizontal forces, that is, surface parallel forces, the surfaces vary while the spacing between the capacitor elements as described above, likewise can vary.

There is preferably provided a multiplicity of main surfaces which are similarly designed and situated equidistantly in a matrix arrangement with respective corresponding main or mating surfaces. With such a measuring assembly, it is possible to measure a three-dimensional force distribution over a large surface, the individual measuring elements or measuring points being entirely mechanically uncouplable from each other.

The assembly will be made particularly light, thin and simple if the capacitor surfaces are designed as thin layers applied to or pressed upon plastic sheets joined to each other by gluing by intercalation of the elastomeric dielectric, the plastic sheets being divided between the capacitor surfaces by notches or grooves. The matrix arrangements thus resulting can be manufactured at very reasonable cost and also as relatively thin "sheets" so that they can be used in shoes as inserted soles. The individual sensor elements are uncoupled from each other by the notches which, when screening surfaces are added to both outer surfaces, also separate them. The notches lead at least up to the elastomeric dielectric or optionally also into a portion thereof.

The sensitivity is especially high when the dielectric is surrounded by a foamed, preferably close-pored, elastomer. But the dielectric preferably consists of two layers which have oppositely directed temperature coefficients, regarding their dielectricity constant, the mechanical dimensioning being such that a common temperature coefficient of substantially zero is obtained. In this manner it is possible to eliminate the effects of temperature upon the individual sensor capacities so that a gauging of the sensors or of a single sensor having been once effected retains its validity over a long test duration despite changing temperatures.

The above and other objects, features and advantages of the invention will become apparent from the following detailed description which is to be read in connection with the accompanying drawings.

DETAILED DESCRIPTION OF THE PREFERRED EMBODIMENTS

Figure 1:
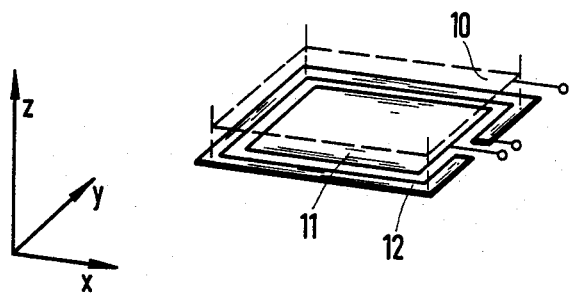
FIG. 1 is a perspective, diagrammatic representation of a first embodiment of the invention.

FIG. 1 is a perspective view which shows a representation of a measurement recorder wherein a large capacitor surface 10 is situated over a smaller capacitor surface 11. Between both surfaces, there is a compressible dielectric so that when a force in the z-direction acts upon the assembly, the capacitor surfaces approximate each other. Around the smaller capacitor surface 11 is situated another capacitor surface 12 which preferably has an outer edge that projects beyond the outer edge of the first capacitor surface 10.

This measuring assembly can be used in different ways. On the one hand, it is possible to ground the surrounding capacitor surface 12 and measure only the capacity between the capacitor surfaces 10 and 11. If there now acts in the x or y direction a force which via shearing forces moves the capacitor surfaces 10 and 11 parallel with each other, there results therefrom no change in the capacity between the surfaces 10 and 11. The active capacitor surface remains actually constant. If the surrounding capacitor surface 12 is not grounded, but the capacity is measured both between the capacitor surface 11 and the capacitor surface 10 and between the capacitor surface 12 and the capacitor surface 10, it is possible from the latter measurement to obtain information concerning the force appearing in the x or y direction.

Figure 2:
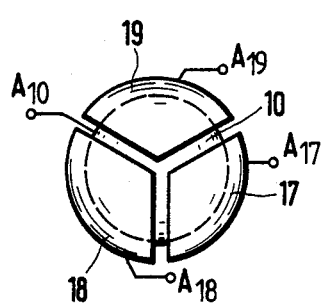
FIG. 2 is a plan view of an assembly according to the invention with three mating surfaces.
Figure 3:
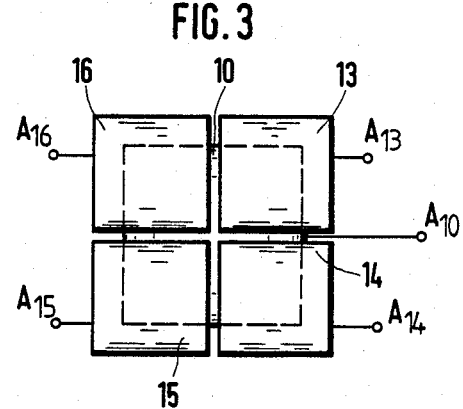
FIG. 3 is a plan view of an assembly according to the invention with four mating surfaces.

In the assemblies shown in FIGS. 2 and 3, the forces in the x or y direction can be more accurately measured. In the assembly of FIG. 2, there is situated opposite to a circular smaller capacitor surface 10, a set of three sector capacitor surfaces 17 to 19 which are electrically separated from each other. The sector surfaces 17 to 19 have a larger external periphery than the capacitor surface 10. If a force in the x or y direction now appears in this measuring assembly, the capacitor surface 10 moves parallel with the sector surfaces 17 to 19 so that the individual capacities change. The change becomes particularly clear when a total of four square mating surfaces 13 to 16 are situated opposite to a smaller capacitor surface 10, as shown in FIG. 3. If in this case, a force in the x direction (seen from left to right in FIG. 3) acts upon the capacitor surface 10 so that the latter is moved relative to the mating surfaces, then the capacities between the capacitor surfaces 15 and 16 and the surface 10 decrease while the capacities between the capacitor surfaces 13 and 14 and the surface 10 increase. From the differential, it is then possible to deduce the magnitudes of the force according to the amount of change.

Simultaneously, if a force acts perpendicular to the capacitor surfaces 10 to 16 that is, in the z direction, then the effect of this force upon the individual capacities must be eliminated from the resultant measurement of the forces in the x and y directions. This is done by allowing a magnitude proportional to the force in the z-direction or to the spacing of the surfaces 13 to 16 from the surface 10 to enter as a standardizing factor in the differential measurement.

Figure 4:
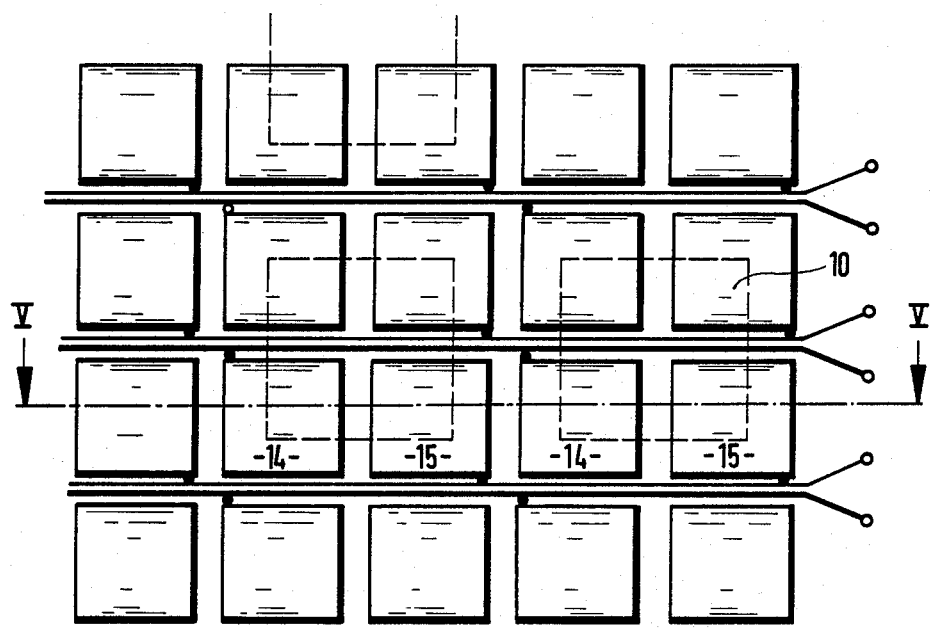
FIG. 4 is a plan view of a matrix arrangement according to the invention with four mating surfaces.

FIG. 4 diagrammatically shows the cutout of a matrix arrangement consisting of elements according to FIG. 3. From FIG. 4, it can be seen that equal capacitor surfaces (producing equal signals) are always electrically combined and connected by a common exterior terminal. For instance, all capacitor surfaces 14 of one row are situated on the same line. The capacitor surfaces 10 are obviously electrically separated by gaps so that each sensor element consisting of four individual capacitors can be separately "selected".

Figure 5:
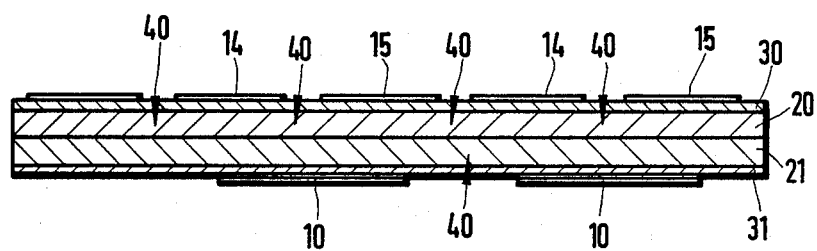
FIG. 5 is a cross-sectional view of FIG. 4, taken along the line V—V Thereof.

From the sectional representation shown in FIG. 5 which is taken along line V—V of FIG. 4, there results another peculiarity of the embodiment shown here. It must be mentioned at the same time that the representation shown in FIG. 5 is in no manner true to scale.

In this embodiment, the capacitor surfaces 10, 14 and 15 are pressed upon sheets 30 and 31. The sheets 30 and 31 are then each glued to a compressible dielectric (elastomer) 20 or 21, the two dielectrics 20 and 21 being connected one upon the other. The dielectrics 20 and 21 have temperature coefficients opposite each other with regard to their electric properties and are dimensioned in a manner such that temperature has no effect on the capacity of the individual capacitors.

The capacitor surfaces 14 and 15, or 10, on sheets 30 and 31 are separated by notches or gaps 40 so that no mechanical coupling can occur via the sheets 30 and 31, between the individual surfaces. In addition, by making notches or grooves, the flexibility of the whole assembly is substantially increased.

Figure 6:
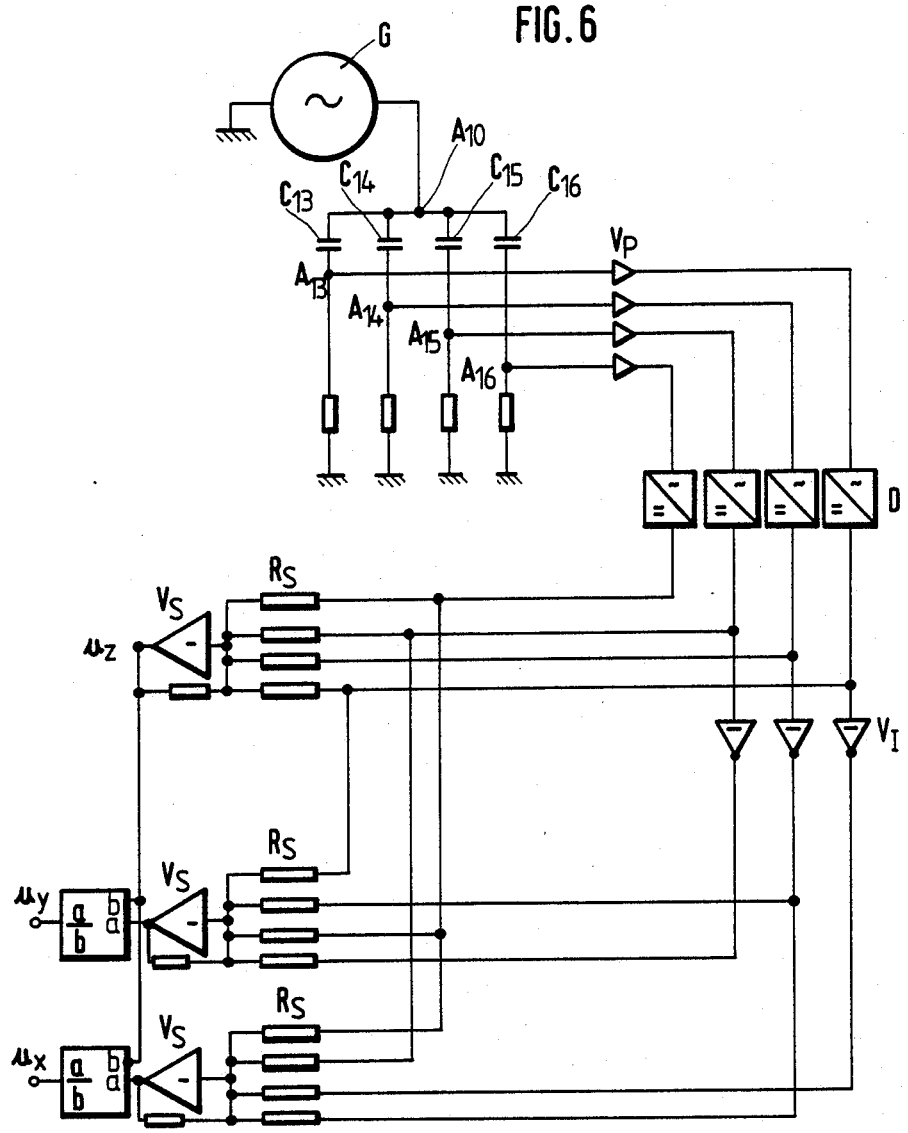
FIG. 6 is a basic circuit for three-dimensional measurement of forces.

FIG. 6 shows a basic circuit for evaluating the measurement signals. Here, a high-frequency generator G applies an alternating current signal to main surface 10 while mating surfaces 13 to 16 are switched to ground via resistances. Thus, four voltage dividers result, consisting of the individual capacities $C_{13}$ to $C_{16}$ and the resistances leading to the ground. The divided voltages are fed via buffer amplifiers $V_p$ to demodulators or A/D converters D, which convert the alternating current signals to direct current signals.

At the outputs of the demodulators D, the measured voltages are summed up via summing resistances Rs and a countercoupled summing amplifier $V_s$ so that there results an output signal Uz that is proportional to the summed capacities. The outputs of the demodulators D are in addition inverted via inverting amplifiers $V_I$.

The values corresponding to the capacities $C_{13}$ and $C_{14}$ are, i addition, jointly counted with the inverted values of the capacities $C_{15}$ and $C_{16}$ via another summing amplifier $V_s$ and summing resistances $R_S$. The sum or differential signal is then divided in a dividing circuit by the summing signal $U_Z$ so that there results a signal Ux proportional to the force acting in the direction on the capacitive measuring assembly according to FIG. 3, the z component being eliminated by the division. The $U_y$ signal corresponding to the direction is produced in an analogous manner, as shown in FIG. 6.

Evidently, the operation of the analogue circuit shown in FIG. 6 can be carried out by a digital system according to a multiplexes of the output signals $A_{13}$ to $A_{16}$.

Figure 8:
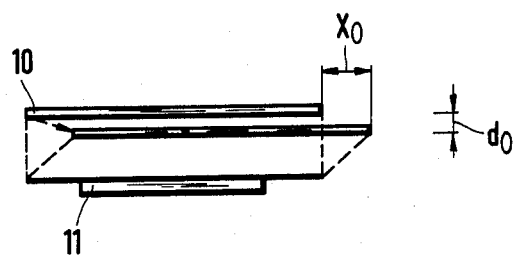
FIG. 8 is an elevational view of the assembly of FIG. 7.
Figure 7:
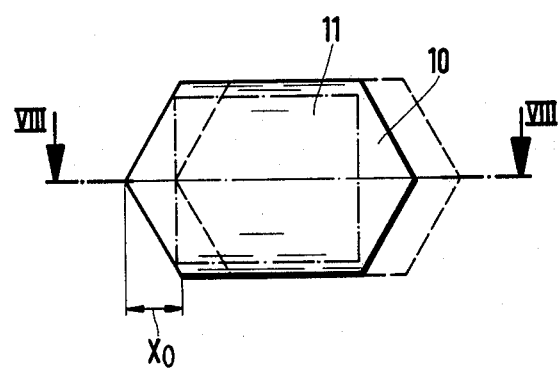
FIG. 7 is a plan view of an assembly according to another embodiment of the invention.

In another preferred embodiment of this invention which falls within the scope of the present invention, there is situated, as shown in FIGS. 7 and 8, opposite to the capacitor surface 11 that has a rectangular shape, a capacitor surface 10 whose outer outline does not coincide with the rectangular outer outline of the capacitor plate 11. For the sake of simplicity, there are drawn in FIG. 7, only two marginal areas of the capacitor plate 10 that project angularly over the capacitor plate 11. The idea here is that, when a vertical force appears, there appears together with the compression of the dielectric a shearing, that is, a horizontal movement of both capacitor plates with respect to each other, that has nothing to do with the compression proper and with the spacing thereby changed between the capacitor plates to effect a change of their capacity. This effect is specially strengthened when there appears in addition to the vertical force a horizontal force, that is, parallel with the capacitor plates. When such a horizontal force appears, the shearing effect is still further strengthened so that there occurs an approximation of the capacitor plates by the factor $d_O$ (FIG. 8) which approximation has nothing to do with the vertical component to be actually measured. To compensate for such parallel displacement or approximation of the plates by the factor $d_O$, there is provided a special molding of the capacitor plate 10. When, for instance, a purely horizontal force acts between the capacitor plates 10 and 11 and therefore moves them, even though the plates approach each other, there is obtained, on the other hand, due to the molding, a reduction of the opposite capacitor surfaces. With an adequate molding, this error can be fully compensated. For the sake of clarity, there is shown here a linear ascent. The corresponding marginal shape of the capacitor plate 10 is obviously kept on all four sides in order that the compensation is effective in all directions in case of horizontal forces.

Having described specific preferred embodiments of the invention with reference to the accompanying drawings, it will be appreciated that the present invention is not limited to those precise embodiments, and that various changes and modifications can be effected therein without departing from the scope or spirit of the invention as defined in the appended claims.

What is claimed is:

1. An assembly for producing signals corresponding to forces and pressures, comprising:

at least three capacitor surfaces situated in two planes substantially opposite to each other;

a dielectric material between the surfaces in the two planes;

the surfaces in one plane being movable relative to the surfaces in the other plane against elastic resetting elements;

one main capacitor surface in one plane lying opposite to all remaining capacitor surfaces in the other plane with intercalation of said dielectric material therebetween and said main surface at least partly covering said remaining surfaces;

said main surface being movable both normally and parallel relative to said remaining surfaces so that forces that act both normally between said main surface and said remaining surfaces and parallel with said capacitor surfaces can be measured or eliminated from separate capacity valves between said main and remaining surfaces; and said remaining surfaces include a smaller surface situated opposite to and completely covered by the main surface and a surrounding surface surrounding said smaller surface, said surrounding surface having an outer edge projecting beyond said main surface so that a differential between capacities of said surrounding surface and said main surface gives a standard for horizontal forces which can be compensated by means of the capacity value between said main surface and said smaller surface in relation to the vertical force component, or vice versa.

2. A measuring assembly according to claim 1, further comprising capacity measuring elements interconnecting said main surface and said remaining surfaces and means for calculating the sum of individual capacities $(C_{13}+C_{14}+C_{15}+C_{16}=K_Z)$ of the capacity measuring elements corresponding to a vertical force ($K_z$) and the sums or differentials of said individual capacities $(C_{13}+C_{14}-C_{15}-C_{16}=K_x; C_{16}+C_{13}-C_{14}-C_{15}=K_y)$ corresponding horizontal forces ($K_x,K_y$) computed on the total capacity or vertical force ($K_x/K_z; K_y/K_z$).

3. An assembly according to claim 1, wherein there is provided a multiplicity of main surfaces and a multiplicity of remaining surfaces that are similarly designed and equidistantly disposed in a matrix arrangement.

4. An assembly according to claim 3, wherein matrix outputs are connected via multiplexer/demultiplexer arrangements with measuring apparatus for determining the individual capacity values.

5. An assembly according to claim 3, wherein said capacitor surfaces are thin layers mounted upon plastic sheets that are joined to each other with intercalation of an elastomeric dielectric material therebetween, said plastic sheets between said capacitor surfaces being separated by notches.

6. An assembly according to claim 1, wherein said dielectric material comprises at least one foamed elastomer.

7. An assembly according to claim 1, wherein said dielectric material comprises at least two planar layers parallel with said surfaces having oppositely directed temperature coefficients and having a thickness such that a total temperature coefficient of the assembly becomes essentially zero.

8. An assembly according to claim 1, further comprising shields above and below said capacitor surfaces with intercalation of a dielectric material therebetween.

9. An assembly for producing signals corresponding to forces and pressures, comprising:
at least three capacitor surfaces situated in two planes substantially opposite to each other;
a dielectric material between the surface in the two planes;
the surfaces in one plane being movable relative to the surfaces in the other plane against elastic resetting elements;
one main capacitor surface in one plane lying opposite to all remaining capacitor surfaces in the other plane with intercalation of said dielectric material therebetween and said main surface at least partly covering said remaining surfaces;
said main surface being movable both normally and parallel relative to said remaining surfaces so that forces that act both normally between said main surface and said remaining surfaces and parallel with said capacitor surfaces can be measured or eliminated from separate capacity valves between said main and retaining surfaces; and
said remaining surfaces including at least three substantially congruous smaller surfaces situated opposite to the main surface, separated from each other and having outer edges projecting beyond the outer edge of said main surface.

10. An assembly according to claim 9, further comprising capacity measuring elements interconnecting said main surface and said remaining surfaces; and
means for calculating the sum of individual capacities ($C_{13}+C_{14}+C_{15}+C_{16}=K_Z$) of the capacity measuring elements corresponding to a vertical force ($k_z$) and the sums or differentials of said individual capacities $C_{13}+C_{14}-C_{15}-C_{16}=K_x$, $C_{16}+C_{13}-C_{14}-C_{15}=K_y$) corresponding to horizontal forces ($K_x,K_y$) computed on the total capacity of vertical force ($K_x/K_z; K_y/K_z$).

11. An assembly according to claim 9, wherein there is provided a multiplicity of main surfaces and a multiplicity of remaining surfaces that are similarly designed and equidistantly disposed in a matrix arrangement.

12. An assembly according to claim 11, wherein matrix outputs are connected via multiplexer/demultiplexer arrangements with measuring apparatus for determining the individual capacity values.

13. An assembly according to claim 11, wherein said capacitor surfaces are thin layers mounted upon plastic sheets that are joined to each other with intercalation of an elastomeric dielectric material therebetween, said plastic sheets between said capacitor surfaces being separated by notches.

14. An assembly according to claim 9, wherein said dielectric material comprises at least one foamed elastomer.

15. A measuring assembly according to claim 9, wherein said dielectric material comprises at least two planar layers parallel with said surfaces having oppositely directed temperature coefficients and having a thickness such that a total temperature coefficient of the assembly becomes essentially zero.

16. An assembly according to claim 9, further comprising shields above and below said capacitor surfaces with intercalation of a dielectric material therebetween.

17. An assembly for producing signals corresponding to forces and pressures, comprising:
at least three capacitor surfaces situated in two planes substantially opposite to each other;
a dielectric material between the surfaces in the two planes;
the surface in one plane being movable relative to the surfaces in the other plane against elastic resetting elements;
one main capacitor surface in one plane lying opposite to all remaining capacitor surfaces in the other plane with intercalation of said dielectric material therebetween and said main surface at least partly covering said remaining surfaces;
said main surface being movable both normally and parallel relative to said remaining surfaces so that forces that act both normally between said main surface and said remaining surfaces and parallel with said capacitor surfaces can be measured or eliminated from separate capacity valves between said main and remaining surfaces;
capacity measuring elements interconnecting said main surface and said remaining surfaces; and
means for calculating the sum of individual capacities ($C_{13}+C_{14}+C_{15}+C_{16}=K_z$) of the capacity measuring elements corresponding to a vertical force ($K_z$) and the sums or differentials of said individual capacities ($C_{13}+C_{14}-C_{15}-C_{16}=K_x$, $C_{16}+C_{13}-C_{14}-C_{15}=K_y$) corresponding to horizontal forces ($K_x,K_y$) computed on the total capacity or vertical force ($K_x/K_z;K_y/K_z$).

18. An assembly according to claim 17, wherein there is provided a multiplicity of main surfaces and a multiplicity of remaining surfaces that are similarly designed and equidistantly disposed in a matrix arrangement.

19. An assembly according to claim 18, wherein matrix outputs are connected via multiplexer/demultiplexer arrangements with measuring apparatus for determining the individual capacity values.

20. An assembly according to claim 18, wherein said capacitor surfaces are thin layers mounted upon plastic sheets that are joined to each other with intercalation of an elastomeric dielectric material therebetween, said plastic sheets between said capacitor surfaces being separated by notches.

21. An assembly according to claim 17, wherein said dielectric material comprises at least one foamed elastomer.

22. A measuring assembly according to claim 17, wherein said dielectric material comprises at least two planar layers parallel with said surfaces having oppositely directed temperature coefficients and having thickness such that a total temperature coefficient of the assembly becomes essentially zero.

23. An assembly according to claim 17, further comprising shields above and below said capacitor surfaces with intercalation of a dielectric material therebetween.

* * * * *